United States Patent [19]

Jautelat

[11] Patent Number: 4,507,496

[45] Date of Patent: Mar. 26, 1985

[54] PROCESS FOR PREPARING 5-SUBSTITUTED 1-CHLORO-3,3-DIMETHYLPENTAN-2-ONES

[75] Inventor: Manfred Jautelat, Burscheid, Fed. Rep. of Germany

[73] Assignee: Bayer Aktiengesellschaft, Leverkusen, Fed. Rep. of Germany

[21] Appl. No.: 613,946

[22] Filed: May 25, 1984

Related U.S. Application Data

[62] Division of Ser. No. 460,687, Jan. 24, 1983.

[30] Foreign Application Priority Data

Feb. 11, 1982 [DE] Fed. Rep. of Germany ....... 3204788

[51] Int. Cl.$^3$ .............................................. C07C 45/59
[52] U.S. Cl. ...................................... 560/266; 568/386
[58] Field of Search ......................... 568/386; 560/266

[56] References Cited

U.S. PATENT DOCUMENTS 2,682,546 6/1954 Copelin ................................ 568/386
3,692,801 9/1972 Robinson et al. .................... 568/386

FOREIGN PATENT DOCUMENTS 2952277 7/1980 Fed. Rep. of Germany ...... 568/386
159505 4/1964 U.S.S.R. .............................. 568/386

Primary Examiner—James H. Reamer
Attorney, Agent, or Firm—Sprung, Horn, Kramer & Woods

[57] ABSTRACT

The invention relates to a process for making 5-substituted 1-chloro-3,3-dimethylpentan-2-ones by reacting a 2-chloromethylene-3,3-dimethyltetrahydrofuran with an acidic compound. The products obtained by the process are useful as intermediates for the provision of fungicidally and antimycotically active compounds.

9 Claims, No Drawings

PROCESS FOR PREPARING 5-SUBSTITUTED 1-CHLORO-3,3-DIMETHYLPENTAN-2-ONES

This is a division of application Ser. No. 460,687, filed 1/24/83.

The present invention relates to a new process for preparing 5-substituted 1-chloro-3,3-dimethylpentan-2-ones which can serve as intermediate products in preparing fungicidally and antimycotically active compounds.

Some 5-substituted 1-chloro-3,3-dimethylpentan-2-ones are known and can be prepared by chlorinating 5-substituted 3,3-dimethylpentan-2-ones [Houben-Weyl, 7/2, page 2162]. They can also be prepared, according to our own proposal (German Patent Application No. P 30 49 461.2 of 30.12.1980), by reacting 1,1-dichloro-3,3-dimethylpent-b 1-end with phenolates.

However, the first process has the disadvantage that in many cases the products are not single compounds, because polychlorination takes place to give dichloro and trichloro ketones. Although the second process can already be used in its present form, not all desirable compounds are accessible in this way. For example, 1,5-dichloro-3,3-dimethylpentan-2-one cannot be obtained in this way, since reaction with phenolates always leads to substitution to give 5-aryloxy derivatives.

It has now been found that previously not easily accessible 5-substituted 1-chloro-3,3-dimethylpentan-2-ones of the formula

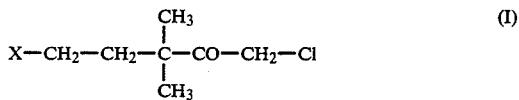

in which

X represents halogen or an acyloxy radical having 1-8 carbon atoms can be prepared in high yields by reacting 2-chloromethylene-3,3-dimethyltetrahydrofuran of the formula

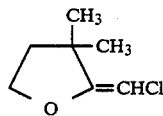

with acidic compounds of the formula

H—X    (III)

in which

X has the abovementioned meaning, at temperatures of 0° C. to 200° C.

It is very surprising that the reaction with hydrogen halides or carboxylic acids does not lead to a 1,2-addition to the double bond, but, instead, the ring opens and 5-substituted 1-chloro-3,3-dimethylpentan-2-ones of the formula I result. The process is therefore of industrial interest.

The process according to the invention has a number of advantages. Thus, the reaction proceeds in high selectivity and yield. The reaction conditions are mild and gentle.

If 2-chloromethylene-3,3-dimethyltetrahydrofuran and hydrogen chloride are used as starting materials, the reaction can be represented by the following equation:

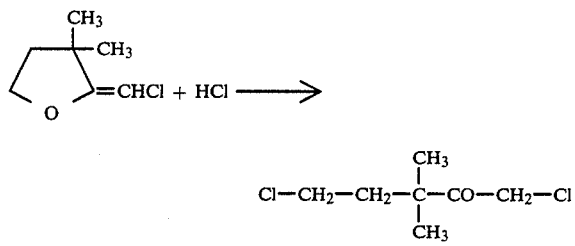

2-Chloromethylene-3,3-dimethyltetrahydrofuran (II) has as yet not been disclosed. It is prepared from 1,1,5-trichloro-3,3-dimethyl-1-pentene, which is known [German Offenlegungsschrift No. 3,029,970], by successive reaction with carboxylates and bases in a one-vessel process according to the following equation:

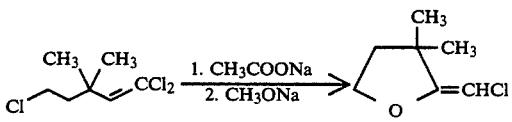

Starting materials of the formula III which are used are generally known. In the formula III, X represents halogen, preferably chlorine, bromine or iodine, or acyloxy (preferably alkanoyloxy, halogenated, particularly chlorinated, alkanoyloxy, benzoyloxy or halogenated, particularly chlorinated benzoyloxy) having 1 to 8 C atoms, preferably formyloxy, acetoxy, chloroacetoxy, benzoyloxy or 2,4-dichlorobenzoyloxy.

The reaction can be carried out not only in the absence but also in the presence of a diluent. Possible diluents are all inert organic solvents; for example hydrocarbons, such as toluene or chlorobenzene, halogenated hydrocarbons, especially halogenated alkanes, such as methylene chloride or chloroform, or ethers, such as 1,2-dimethoxyethane or dioxane.

The reaction temperature can be varied within a relatively wide range. In general, the reaction is carried out between 0° and 200°, preferably between 20° and 150°. The reaction can be carried out not only under normal pressure in an open system but also under pressure in an autoclave. The pressure can be varied within a range of 1 to 100 bar. Possible catalysts, preferably in the reaction with carboxylic acids, are strongly acidic materials, such as mineral acids, for example sulphuric acid or hydrochloric acid; sulphonic acids, such as methanesulphonic acid or p-toluenesulphonic acid; strong carboxylic acids, such as trifluoroacetic acid or a Lewis acid, such as aluminium chloride. The catalysts are only used in amounts of 0.1 to 5%.

In carrying out the process according to the invention, 1 to 3 equivalents of the acidic compound of the formula III, preferably 1 to 2 equivalents, are used per one equivalent of the starting material II. However, the acidic compound can also be used as a diluent.

1,5-Dichloro-3,3-dimethylpentan-2-one, which is accessible by the process according to the invention, is an intermediate product suitable for preparing fungicidally and antimycotically active azole derivatives. If, for example, it is reacted with a phenol of the formula

H—O—R in which

R represents optionally substituted phenyl chloroether-ketones of the formula

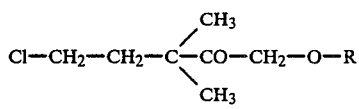

are obtained.

Their conversion, after halogenation, leads, together with imidazole or 1,2,4-triazole in the presence of a diluent and of an acid-binding agent, to azolylphenoxytetrahydrofuran-2-ylidenemethanes of the formula

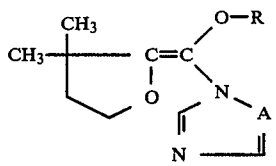

in which

A represents a nitrogen atom or the CH group and
R represents optionally substituted phenyl.

Of these, for example (4-chlorophenoxy)-(imidazol-1-yl)-3,3-dimethyltetrahydrofuran-2-ylidenemethane, melting point: 85°–88° C., and (4-fluorophenoxy)-(imidazol-1-yl)-3,3-dimethyltetrahydrofuran-2-ylidenemethane, melting point: 214° C., are distinguished by very powerful antimycotic actions.

EXAMPLE 1

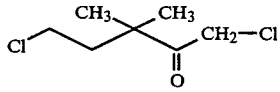

A fast stream of hydrogen chloride gas is passed from a pressure cylinder into ice-cooled 476 g (3.25 mols) of 2-chloromethylene-3,3-dimethyltetrahydrofuran. All of the gas is absorbed, and the internal temperature rises to 30°. After the reaction mixture has been completely saturated with hydrogen chloride, it is stirred for 2 hours at room temperature. Excess hydrogen chloride is first distilled off under a water-jet vacuum, and then a distillation in a high vacuum is carried out. 531 g (2.93 mols, 90%) of 1,5-dichloro-3,3-dimethylpentan-2-one are obtained with a boiling point of 85°–90°/0.3.

NMR (CDCl$_3$): δ 1.25 (s, 6H), 2.1 (t, 2H), 3.5 (t, 2H), 4.4 (s, 2H).

EXAMPLE 2

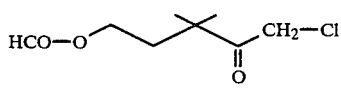

29.2 g (0.2 mol) of 2-chloromethylene-3,3-dimethyltetrahydrofuran, in 100 ml of formic acid, are heated at 60° for 5 hours. Fractional distillation produces 34 g (0.174 mol, 87%) of 1-chloro-3,3-dimethyl-5-formyloxypentan-2-one with a boiling point of 110°/0.2.

NMR (DCDl$_3$): δ 1.25 (s, 6H), 2.0 (t, J=7 Hz, 2H), 4.2 (t, J=7 Hz, 2H), 4.45 (s, 2H), 8.0 (s, 1H).

EXAMPLE 3

Preparation of the starting material 2-chloromethylene-3,3-dimethyltetrahydrofuran of the formula

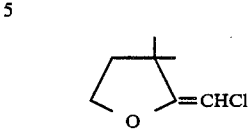

806 g (4 mols) of 1,1,5-trichloro-3,3-dimethyl-1-pentene are heated under reflux for 6 hours together with 360 g (4.4 mols) of anhydrous sodium acetate in 1 liter of dimethylformamide. When the reaction mixture has cooled down to about 100°, 1.6 liters (8 mols) of 30% sodium methylate solution in methanol are added dropwise, and the mixture is heated under reflux for a further 4 hours. The cold solution is poured into water, and the mixture is repeatedly extracted with methylene chloride. When the solution has been dried and the solvent driven off, 654 g of product remain which are fractionated over a column. 522 g (3.56 mols, 89%) of 2-chloromethylene-3,3-dimethyltetrahydrofuran are obtained with a boiling point of 84°–87°/20.

NMR (CDCl$_3$): δ 1.2 (s, 6H), 1.9 (t, J=6.5 Hz), 4.15 (t, J=6.5 Hz, 2H), 4.85 (s, 1H).

What is claimed is:

1. Process for preparing 5-substituted 1-chloro-3,3-dimethylpentan-2-ones of the formula

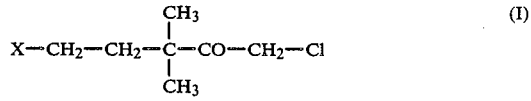

in which

X represents a halogen or an acyloxy radical having 1–8 carbon atoms, which comprises reacting 2-chloromethylene-3,3-dimethyltetrahydrofuran of the formula

with an acidic compound of the formula

in which

X has the abovementioned meaning, at a temperature of 0° to 200° C.

2. Process according to claim 1, wherein the reaction is carried out in the presence of a diluent.

3. Process according to claim 1, wherein an inert organic solvent is used as the diluent.

4. Process according to claim 1, wherein the reaction is carried out in the presence of a catalyst.

5. Process according to claim 4, wherein a mineral acid, sulphonic acid, strong carboxylic acid or Lewis acid is used as catalysts.

6. Process according to claim 5, wherein the catalyst is used in an amount of 0.1–5%.

7. Process according to claim 1, wherein the reaction is carried out at 20°–150° C.

8. Process according to claim 1, wherein hydrogen chloride is used as the acidic compound.

9. Process according to claim 1, wherein formic acid is used as the acidic compound.

* * * * *